United States Patent [19]

Huizinga et al.

[11] 4,328,280

[45] May 4, 1982

[54] SUPPRESSION OF SPARK DISCHARGES FROM NEGATIVELY TRIBOELECTRICALLY CHARGED SURFACES

[75] Inventors: John S. Huizinga; John Stevens, both of Harlow, England

[73] Assignee: Minnesota Mining and Manufacturing Company, St. Paul, Minn.

[21] Appl. No.: 38,698

[22] Filed: May 14, 1979

[30] Foreign Application Priority Data

May 15, 1978 [GB] United Kingdom ............... 19554/78

[51] Int. Cl.³ ........................ G03C 1/82; B32B 27/36; B32B 9/00
[52] U.S. Cl. ........................... 428/411; 260/DIG. 15; 428/480; 428/537; 428/913
[58] Field of Search ............... 428/537, 913, 480, 411; 430/527, 528, 529; 260/DIG. 15

[56] References Cited

U.S. PATENT DOCUMENTS

| | | | |
|---|---|---|---|
| 3,264,108 | 8/1966 | Mackey | 430/529 |
| 3,850,642 | 11/1974 | Bailey | 430/528 |
| 3,884,699 | 5/1975 | Cavallo | 430/527 |
| 3,887,377 | 6/1975 | Yamamoto | 430/529 |
| 4,039,521 | 8/1977 | Smith | 430/171 |

*Primary Examiner*—Ellis P. Robinson
*Attorney, Agent, or Firm*—Cruzan Alexander; Donald M. Sell; Mark A. Litman

[57] ABSTRACT

The generation of electrostatic charges and spark discharging when surfaces having different work functions are contacted is a well known phenomenon. Spark discharging can be suppressed according to the present invention by the application of isopropylbenzene derivatives to one of the surfaces.

10 Claims, No Drawings

SUPPRESSION OF SPARK DISCHARGES FROM NEGATIVELY TRIBOELECTRICALLY CHARGED SURFACES

This invention relates to the suppression of spark discharges from negatively triboelectrically charged surfaces.

When two surfaces with different work functions are brought into contact, charging takes place. The resulting electrostatic charges are due to the transfer of electrons to the surface with the numerically greater work function. This gives that surface a negative charge and leaves a positive charge on the other surface. As a result of this charging of the surfaces, spark discharges occur and in many circumstances these discharges have serious disadvantages. Thus, for example, photographic films will show discharge marks if spark discharges occur during the manufacture or processing of the sensitive film, particularly when it is passed over rollers or the like. Explosions can result if there are spark discharges within an explosive atmosphere.

Contact charging can be avoided if all contacting surfaces have the same work function. However this requires total control of the environment and is normally impracticable.

A usual method for the elimination of static charges is to provide a conducting pathway for neutralization of the charge. For example, insulating surface may be coated with an ionic salt which, by absorbing water from the atmosphere, will give increased surface conductivity. The major disadvantage of this method is that neutralization of the charge is a slow process and a spark discharge can occur if the rate of charge increase is faster than the rate of charge neutralization. Other methods relying upon neutralization of a charged surface by ionization of a gas in contact with the surface suffer from the same disadvantage. In addition, these methods require the use of a corona bar or an ionizing radioactive source, again implying a large degree of environmental control.

SUMMARY OF THE INVENTION

According to one aspect of the invention there is provided a method of suppressing spark discharges from a surface liable to be or become negatively charged. In the present invention, a surface is treated with an isopropylbenzene carrying a substituent with a Hammett $\sigma_p$ constant of from $-0.17$ to $+0.82$ in the 2— or 4— position relative to the isopropyl group or a substituent with a Hammett $\sigma_m$ constant of from 0.0 to $+0.88$ in the 3— position relative to the isopropyl group.

Unexpectedly, surfaces treated according to the invention with an isopropylbenzene derivative have a reduced tendency to spark discharge when they are carrying a negative triboelectric charge. The treatment of a surface with an isopropylbenzene derivative does not prevent a negative charge from forming on the surface nor discharge a negative charge formed on that surface. Instead it suppresses spark discharges from that surface. The treatment may be a direct application of the derivative or the derivative in a binder such as a gelatin top coat.

If electrical breakdown is induced by bringing a probe near the surface, then less charge is dissipated with a surface treated according to the invention than with an untreated surface. The invention is not effective in the treatment of surfaces carrying a positive triboelectric charge, but in many cases spark discharges from positively charged surfaces are less disadvantageous than those from negatively charged surfaces.

Although we are not certain, we believe that the mode of action of the invention is as follows. The electrons forming a negative triboelectric charge on a surface are assumed to occupy antibonding orbitals of the surface molecules. In most cases, the molecules at the surface of an electrically insulating material cannot polarize and the excess electrons are maintained at a high energy. If the excess electrons can react with a free radical generator at the surface, then the energy of the excess electrons may be significantly reduced by the formation of a negatively charged ion by chemical reaction. This should lead to a reduction in the probability of electrons leaving the negatively charged surface and a decrease in mobility of negative charge. It is known that hydrocarbons with tertiary centers undergo oxidation in contact with air to give unstable hydroperoxides. Further it is known that hydrocarbon hydroperoxides can decompose with the formation of free radicals in particular to give hydroxyl radicals.

The relevance of this consideration was tested by examining the effect of coating a surface with a sample of cumene from which any peroxide had been removed by washing with a solution of ferrous sulphate and then distilling under vacuum. The sample did not show any suppression of sparking when tested immediately after coating. After leaving the surface coated with this sample of cumene in air for 48 hours, spark suppression activity was found. Furthermore, treating a surface with cumene hydroperoxide also showed spark suppression immediately. It therefore appears that the presence of cumene hydroperoxide is important to the action of spark suppression.

In order to use the electrostatic charge retaining properties of the isopropylbenzene derivatives described above to the best effect, it is necessary that the treated surface should become negatively charged by contact electrification.

In another aspect of this invention, this feature can be achieved in a wide range of situations by using the isopropylbenzene derivative in combination with a fluorocarbon derivative. In certain cases the isopropylbenzene derivative may carry a fluorocarbon group as part of a substituent group, so fulfilling both requirements in one material. In these ways one can ensure negative contact electrification of the treated surface under the intended conditions of use.

Similarly, since the isopropylbenzene derivatives are only effective when used on the surface of a negatively charged material, it may be desirable when treating a liquid or gel to incorporate a substituent group which confers surfactant properties on the molecule. This will allow the active agent to concentrate at the surface of a liquid or gel and so the surface of a liquid or gel can be protected from spark discharges by the action of the isopropylbenzene derivative.

The isopropylbenzene derivative can also possess an ionic center, a fluorocarbon residue, a surfactant group or any combination thereof. The fluorocarbon residue can ensure negative contact electrification, the ionic center can confer conduction of charges formed, and the surfactant group can ensure uniform spreading of the derivative on the surface, these properties individually or together being in every case associated with the spark suppression properties of the isopropylbenzene derivative itself.

The invention also extends to surfaces treated with one of the isoproplybenzene derivatives. The invention also extends to a composition for application to a surface liable to be or become negatively charged comprising an isopropylbenzene derivative with or without a volatile solvent, the derivative carrying a substituent with a Hammett $\sigma_p$ constant of from 0.17 to +0.82 in the 2- or 4- position relative to the isopropyl group or a substituent with a Hammett $\sigma_m$ constant of from 0 to +0.88 in the 3- position relative the isopropyl group.

The invention has particular application to reducing spark discharges from photographic films and in particular to radiographic photographic films. An isopropylbenzene derivative coated on the surface of the film reduces static marks arising from negative contact electrification. It is desirable that the derivative be soluble in water so that it can be applied in a gelatin solution in a conventional coating process. Desirably the derivative has surfactant properties so that it can be concentrated at the surface of the dried gelatin layer. A good derivative from these points of view is P-1-(4-isopropylphenyl)-ethylammoniumperfluorooctylsulphonate. This derivative reacts with formaldehyde and so it is preferable not to use formaldehyde or formaldehyde forming hardeners for the gelatin; instead the gelatin can be hardened, for example, with bis(chloroethylsulphonylmethane).

P-1-(4-isopropylphenyl)-ethylammoniumperfluorooctylsulphonate is a new compound and forms another aspect of the invention. The generic formula below represents the novel compounds of this class

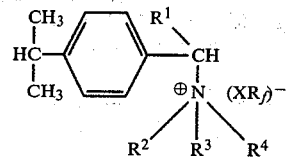

wherein $R^1$ to $R^4$ are independently H or lower alkyl ($C_1$ to $C_5$) and $R_f$ is a highly fluorinated aliphatic radical, preferably a perfluorinated alkyl radical. The term highly fluorinated aliphatic or alkyl radical is well known in the art as represented by U.S. Pat. No. 4,039,521 and the definition of highly fluorinated aliphatic and alkyl groups is hereby incorporated into this application. It is preferred that at least two of $R^2$, $R^3$ and $R^4$ are lower alkyl, and X is —COO— or —SO_3—.

The results obtained with isopropylbenzene can also be achieved with a number of substituted isopropylbenzenes. The efficacy of substituted isopropylbenzenes in the modification of the spark discharge characteristics of negatively charged surfaces is related to the electron withdrawing effect characterized by possessing a Hammett $\sigma_p$ function between −0.17 and +0.82 when in the 4-position and $\sigma_m$ function between 0 and +0.88 when in the 3-position relative to the isopropyl group, give the desired effect. The Hammett functions are not used in a rate controlling sense in this context, but they afford a convenient method of defining the useful range of substituents. Further, it is assumed that in general the effect of a functional group isolated from the benzene ring by at least one methylene group will have a substituent effect closely comparable to that of an alkyl group.

Examples of isopropylbenzene derivatives which suppress spark reduction in a manner according to the invention are listed in the following Table 1.

TABLE 1 isopropylphenyl structure (para or ortho substituted):

| R | σ para | R | σ para |
|---|---|---|---|
| —CH₃ | −0.17 | —NH.CO.CH₃ | 0.0 |
| —CH₂COOH | −0.17 | —NH.CO.CH=CH₂ | 0.0 |
| —(CH₂)₁₀COOH | −0.17 | —NH.SO₂.C₆H₄CH₃ | 0.0 |
| —CH(CH₃)OH | −0.17 | S.CH₂CH₂OH | +0.03 |
| —CH((CH₂)₁₆CH₃)OH | −0.17 | O.CO.CH=CH₂ | 0.31 |
| —CH(CH₃)NH₂ | −0.17 | —C(=NOH)CH₃ | 0.50 |

TABLE 1-continued

Structures shown:

$$\underset{\text{(para)}}{\overset{H_3C\diagdown_{CH}\diagup^{H_3C}}{\underset{R}{\bigcirc}}} \quad \text{or} \quad \underset{\text{(ortho)}}{\overset{CH_3\diagdown_{CH}\diagup^{CH_3}}{\underset{}{\bigcirc}\text{-}R}}$$

| R | σ para | R | σ para |
|---|--------|---|--------|
| $-CH\overset{CH_3}{\underset{NHCO.CH_3}{\diagdown}}$ | −0.17 | $-C\overset{N.NH.C_6H_5}{\underset{CH_3}{\diagup\diagdown}}$ | 0.50 |
| $-CH\overset{CH_3}{\underset{NHSO_2C_6H_4CH_3}{\diagdown}}$ | −0.17 | $-CH-(CH_2)_{16}CH_3$<br>$-CO-CH_2Cl$ | 0.50<br>0.50 |
| $-CH\overset{CH_3}{\underset{NHSO_2C_8F_{17}}{\diagdown}}$ | −0.17 | $-CO-(CH_2)_2COOH$<br>$-CO-CH_3$ | 0.50<br>0.52 |
| $-nC_{12}H_{25}$ | −0.15 | $-CO-CH_2\overset{\oplus}{N}(CH_3)_2(CH_2)_3$<br>$C_8F_{17}.SO_2-NCH_3$ | 0.502 |
| −H | 0.0 | $\overset{\oplus}{-}N(CH_3)_3$ | 0.820 |

A similar range of isopropylbenzene derivatives with a substituent in the 3-position having a Hammett $\sigma_m$ constant of from 0 to +0.88 are also suitable. Suitable substituents include a methyl group which has a Hammett $\sigma_m$ value at the lower end of the range and a quaternized amino group having a Hammett $\sigma_m$ value at the top end of the range.

The Hammett constants of various substituents are exemplified in *Rates and Equilibria of Organic Reactions*, J. E. Leffler and E. Grunwald; J. Wiley, 1963.

In addition to the modification of spark discharge characteristics claimed as the novel feature of this disclosure, specific compounds may also incorporate an ionic center as in a conventional antistat compound or they may incorporate surfactant groups or all of these functions may be combined in one compound.

It is believed that the active chemical agents are the hydroperoxides of the isopropylbenzene derivatives, and that they are formed on the surface by aerial oxidation. The hydroperoxides are unstable dangerous materials and thus are unsuitable for direct application as a pure material to the surface to be treated. The isopropylbenzene derivatives of this invention on the other hand are stable and easily handled.

For substituents in the 2-position relative to the isopropyl group, the range is apparently limited by steric effects. For example, diphenylmethane, 1,3,5-tri-isopropylacetophenone and cyclohexylbenzene do not show any effect upon the spark discharge from negatively charged surfaces.

The spark suppression activity is not a function of the hydroperoxide group alone. Aerated toluene, 1,4-xylene, 1,4-di-isopropylbenzene, and 1,3,5-tri-isopropylbenzene do not give the effect. Furthermore, tert-butylhydroperoxide, isopropylbenzene peroxide and cyclohexane peroxide are not active. Polystyrene does not show the effect, but the oxygen absorption of polystyrene is very low and presumably hydroperoxides are not formed (R. B. Mesrobian and A. V. Tobolsky, J. Polymer Sci. 2,477 (1947)).

The invention will now be illustrated by the following Examples.

EXAMPLE 1

Preparation of N[1-(4-isopropylphenyl)ethyl]perfluorooctylsulphonate.

A solution of (4-isopropylphenyl)ethylamine (16.3 g) in acetone (50 ml) was added slowly to a vigorously stirred supension of perfluoro-octylsulphonyl fluoride (50.3 g) in acetone (100 ml) and triethylamine. The temperature rose to 35° C. and was maintained by controlling the rate of addition. The reaction mixture became clear as the reaction proceeded and became light brown. The solution was stirred for a further 1 hour before evaporating to dryness. The residue was washed with water and the organic residue extracted with ether (200 ml). The ether layer was dried carefully with magnesium sulphate and evaporated on a rotary film evaporator to a brown syrup. Chloroform (100 ml) was added and the solution was evaporated at atmospheric pressure to a pot temperature of 63° C. After storing at 0° C. overnight the product crystallized as yellow needles. These were recrystallized from toluene, with charcoaling, as colourless fluffy crystals of P1-(4-isopropylphenyl) ethyl ammonium perfluoro-octylsulphonate, m.p. 158° C. (38 g, 59%). $C_{19}H_{16}F_{17}NO_2S$ requires: C, 35.36; H, 2.50; N 2.16%. Found C 34.31; H 2.50; N 2.16% NMR data 5% solution in DMSO($d_6$) 1.21 (1H) quintet (J=7 Hz), 1.51 (3H) doublet (J=7 Hz), 2.9 (1H) doublet (J=7 Hz), 4.40 (2H) doublet (J=7 Hz), 7.34 (4H) singlet, 8.2 (1H) broad singlet.

EXAMPLE 2

The apparatus used to examine the charging characteristics and incidence of spark discharges consisted of a driven earthed stainless steel roller in contact with a spring loaded non-metallic roller. A sheet of material was passed between the rollers and collected in a tray. The charge on the surface of the material was detected by an electrometer probe. The surface of the non-metallic roller could be modified by wrapping a sheet of material round it so that the surface in contact with the material under examination can present a different work function. Under these conditions the resultant charge or a spark discharge occuring during the roller process could be detected. The spark discharges may be detected by the characteristic tearing noise, by a radio receiver sensitive to amplitude modulated radio signals or by visual examination of the process in a darkened room. A very reliable method for the detection and recording of spark discharges, however, is to use a sheet of photographic film possessing a high sensitivity to blue light. A piece of such a film, when passed between the rollers in a darkroom with an appropriate safelight and then developed and fixed in a conventional manner, showed heavy black marks due to exposure of the light sensitive material by the light emitted during an electrical discharge. It was found that the polarity of the static charge induced on the film during the rolling process was distinguished by the type of marking. A negative static potential on the surface of the photographic film gave rise to sharp dense images exactly analogous to a picture of a lightening flash. A positive static potential on the surface of the photographic film gave diffuse formless images clearly differentiated from the marks due to discharge at a negative charged surface.

In a typical experiment, the surface of a photographic film possessing a high sensitivity to blue light was sprayed on both sides with a solution of isopropylbenzene in ethanol to give a coating weight of approximately 0.1 g/m$^2$. The spraying was performed under safelight conditions to avoid exposing the photographic film to extraneous light. When the treated film was dry to the touch, it was rolled in the apparatus described above using a non-metallic roller which was known to impart a negative electrostatic charge to the surface of the film. After processing, the film was completely free from the characteristic images due to electrical discharges during the rolling process or the subsequent photographic processing.

For comparison, a sheet of photographic film was sprayed with ethanol and dried under the same conditions. Subsequent rolling and processing were exactly as for the treated film but this film showed the characteristic lightening-flash marking due to electrical discharges.

When a sheet of film treated with isopropylbenzene in the manner described was rolled with a material known to impart a positive electrostatic charge, subsequent processing showed the diffuse markings comparable to the marks obtained on a sheet of untreated film.

EXAMPLE 3

A piece of polyester film base was cleaned with isopropanol and divided into three portions. The first portion was left as the untreated sample, the second portion was coated on both sides with 4-isopropylacetophenone at approximately 1 g/m$^2$ and the third portion was coated on both sides with acetophenone at approximately 1 g/m$^2$ as a control for the spark suppression effect. Subbed film base was used to give a more even coating of the additives. Samples for the Stati-Tester were prepared with a standard punch.

The samples were charged on an MK Stati-Tester Model 169 at 10 μA on the 1 KV range for 12 seconds. The fall in surface voltage after 20 seconds decay in darkness was measured and the results are shown in Table 2. The results of measurement on the Keithley adaptor are also shown in Table 2. In general, the Stati-Tester is more useful for measuring high surface resistivity and hence longer time constants. The Keithley resistivity adaptor is useful for measurements up to $10^{14}$ ohms/sq.

TABLE 2

Conditions:
Charging 12 seconds 10 μA 1 KV. Decay 20 seconds in darkness.
Relative Humidity 42%
Surface resistivity measured on Keithley 6105 Adaptor at 25% RH

| | | Fall in surface Potential from 700V over a 20 second period. | |
|---|---|---|---|
| Material | Surface Resistance Ohms/square | Negative Charge | Positive Charge |
| 1. Polyester Base | $6.6 \times 10^{14}$ | 18V ± 4V | 40V ± 11V |
| 2. Polyester Base + 4-isopropylacetophenone | $6.5 \times 10^{14}$ | 7V ± 3V | 12V ± 6V |
| 3. Polyester Base + Acetophenone | $6.5 \times 10^{14}$ | 16V ± 5V | 17V ± 5V |

The results show that the effect of the surface treatment which results in spark suppression cannot be ascribed to an increase in surface conductivity.

The reproductibility of the tests is improved by using pure additives and a low humidity environment.

The effect has been demonstrated only on surfaces carrying a limited charge. If electron flow is maintained by an external supply the spark suppression effect can be saturated. The minimum applied potential causing sparks from a metal surface to a grounded point is not affected by treating the surface with the derivative.

Obviously, if the potential gradient at the surface causes ionization of the gas in contact with the surface, some neutralization of the charge must occur. Trapping of the negative charge prevents the current flow necessary to sustain a spark discharge. The extent of neutralization under these conditions is probably less than by spark discharge.

EXAMPLE 4

Sheets of double coated silver halide photographic film similar to medical X-ray film in blue light sensitivity, were sprayed on both sides with the following materials in ethanol solution to give approximately 0.1 g/m$^2$ of active component on the surface. The sheets were then immediately passed through the charging rollers described in Example 2 under conditions giving negative charge accumulation on the untreated film sheet and suitable safelights to prevent fogging of the film. The following results were obtained after processing the sheets in a normal developer and fix sequence.

| Active Agent | Result |
|---|---|
| None | heavy "tree static" marks |
| Freshly distilled isopropylbenzene | heavy "tree static" marks |
| Freshly distilled isopropylbenzene but film left for 48 hours in dark before testing. | no static marks |

| Active Agent | Result |
|---|---|
| -continued | |
| Freshly distilled isopropylbenzene through which air had been bubbled for 1 hour in daylight | no static marks |
| Undistilled isopropylbenzene which had been kept on stock shelves for several months | no static marks |

The results indicate that the presence of hydroperoxides in the isopropylbenzene is necessary to obtain the spark suppression effect.

EXAMPLE 5

The spark suppression properties of compounds of formula (I) were tested in a gelatin top coat applied to a photographic film.

The apparatus used to examine the charging characteristics and incidence of spark discharges was as described in Example 1.

The marks visible on each film were visually graded according to the scale 0 to ±5. The zero value was accorded to films with no marks and 5 to a film bearing many marks rendering the film unsuitable for use. A positive sign represents marks attributed to positive static potential and a negative sign to marks attributed to negative static potential.

The following Table 3 reports the results of the tests conducted by rolling the film at 25% relative humidity with the spark suppression additives in the top coat. The isopropylbenzene compounds were prepared in accordance with our Patent Application of even date. Compounds of the invention were compared with known compounds used for the reduction of static in photographic films as disclosed in U.S. Pat. No. 3,850,642.

TABLE 3

| Additive | Quantity (ml) of 4% aqueous solution of additive per 100 g of top coat gel | Static marking |
|---|---|---|
| (Comparison) $(CH_2)_3\overset{\oplus}{N}(CH_2)_3NSO_2C_8F_{17}CL^{\ominus}$ H | 3 | −4 |
| 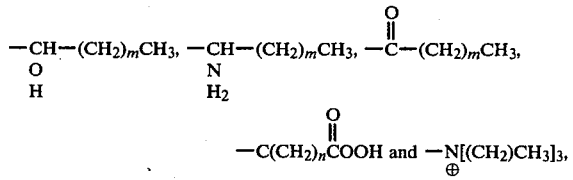 $C_8F_{17}SO_3^{\ominus}$ | 1 | −4 |
| | 3 | −3 |
| | 10 | 0 |
| | 30 | 0 |
| | 100 | −2 +1 |
| 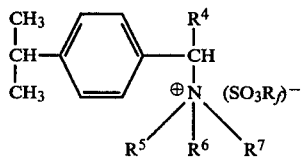 $C_8F_{17}SO_3^{\ominus}$ | 1 | −3 |
| | 3 | −4 |
| | 10 | −2 |
| | 30 | 0 |
| | 100 | −2 |

EXAMPLE 6

Adopting the procedures according to Example 4 a sheet of film was treated with 96% isopropylbenzene hydroperoxide to give 0.1 g/m² on the film surface.

After immediate treatment through the charging rollers followed by photographic processing, no signs of static marks were found. This confirms the hydroperoxide as the agent giving spark suppression.

We claim:

1. A method of suppressing spark discharge from a surface which is capable of becoming negatively triboelectrically charged which comprises applying to said surface an isopropylbenzene compound having a substituent in the 2- or 4-position relative to the isopropyl group which has a Hammett $\sigma_p$ constant of from −0.17 to +0.82 or a substituent in the 3-position relative to the isopropyl group which has a $\sigma_m$ constant of from 0.0 to +0.88.

2. The method of claim 1 wherein said isopropylbenzene compound is represented by the formula:

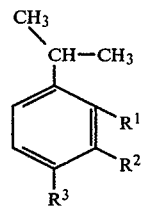

wherein $R^1$ and $R^3$ are selected from the class consisting of H, alkyl, $-(CH_2)_nCOOH$, $$-\underset{\underset{H}{O}}{CH}-(CH_2)_mCH_3, -\underset{\underset{H_2}{N}}{CH}-(CH_2)_mCH_3, -\overset{O}{\underset{\|}{C}}-(CH_2)_mCH_3,$$

$$-\overset{O}{\underset{\|}{C}}(CH_2)_nCOOH \text{ and } -\overset{\oplus}{N}[(CH_2)CH_3]_3,$$

wherein n is 1 to 20 and m is 0 to 20, and $R^2$ is selected from H, alkyl of 1 to 20 carbon atoms and quaternary amino groups.

3. The method of claim 1 in which the isopropylbenzene compound has the formula:

$$\underset{CH_3}{\overset{CH_3}{\underset{|}{CH}}}-\underset{}{\text{(benzene)}}-\underset{\underset{R^5}{\overset{|}{\underset{R^6}{\overset{\oplus}{N}}}}{\overset{R^4}{\underset{|}{CH}}}}(SO_3R_f)^-$$

wherein $R^4$, $R^5$, $R^6$ and $R^7$ are independently selected from $H^1$, and alkyl of 1 to 5 carbon atoms and $R_f$ is a highly fluorinated aliphatic group of 1 to 20 carbon atoms.

4. The method of claim 3 in which $R_f$ is a perfluoroalkyl group.

5. A surface capable of being negatively triboelectrically charged which has coated and dried thereon an isopropylbenzene compound having a substituent in the 2- or 4- position relative to the isopropyl group which has a Hammet $\sigma_p$ constant of from −0.17 to +0.82 or a substituent in the 3-position related to the isopropyl group which has a $\sigma_m$ constant of from 0.0 to +0.88.

6. The method according to claim 2 wherein said compound is capable of forming hydroperoxides by aerial oxidation.

7. The method according to claim 3 wherein said compound is capable of forming hydroperoxides by aerial oxidation.

8. A surface according to claim 5 wherein said compound is capable of forming hydroperoxides by aerial oxidation.

9. The method according to claim 1 wherein said compound is capable of forming hydroperoxides by aerial oxidation.

10. The method according to claim 4 wherein said compound is capable of forming hydroperoxides by aerial oxidation.

* * * * *